(12) United States Patent
Brothers et al.

(10) Patent No.: US 6,177,196 B1
(45) Date of Patent: Jan. 23, 2001

(54) PHOSPHORUS-CONTAINING FLUOROMONOMERS AND POLYMERS THEREOF

(75) Inventors: Paul Douglas Brothers, Chadds Ford, PA (US); Ming-Hong Hung; Michael Joseph Michalczyk, both of Wilmington, DE (US); Tatsuhiro Takahashi, Kanagawa (JP)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/255,901

(22) Filed: Feb. 23, 1999

Related U.S. Application Data

(62) Division of application No. 08/929,216, filed on Sep. 9, 1997, now Pat. No. 5,969,067.
(60) Provisional application No. 60/026,023, filed on Sep. 13, 1996.

(51) Int. Cl.$^7$ ............................. B32B 27/28; B32B 27/30
(52) U.S. Cl. ......................... 428/422; 428/421; 428/447; 428/450; 428/451; 428/457; 428/461; 428/500
(58) Field of Search ................................... 428/422, 421, 428/447, 500

(56) References Cited

U.S. PATENT DOCUMENTS

| | | | |
|---|---|---|---|
| 4,281,091 | 7/1981 | Strazik et al. | 525/518 |
| 4,281,092 | 7/1981 | Breazeale | 526/247 |
| 4,564,717 | 1/1986 | Ohmori et al. | 568/843 |
| 5,059,720 | 10/1991 | Hung | 568/674 |
| 5,266,639 | 11/1993 | Chapman et al. | 525/200 |
| 5,328,946 | 7/1994 | Tuminello et al. | 524/462 |
| 5,397,829 | 3/1995 | Morgan et al. | 524/463 |

*Primary Examiner*—Fred Zitomer
(74) *Attorney, Agent, or Firm*—Thomas W Steinberg

(57) ABSTRACT

Fluorinated vinyl ethers having phosphorus-containing groups are useful as monomers in making fluoropolymers having functional sites.

7 Claims, No Drawings

PHOSPHORUS-CONTAINING FLUOROMONOMERS AND POLYMERS THEREOF

RELATED APPLICATION

This is a division of Application No. 08/929,216 filed Sep. 9, 1997, now U.S. Pat. No. 5,969,067.

This application claims the benefit of priority of Provisional Application Serial No. 60/026,023 filed Sep. 13, 1996.

FIELD OF THE INVENTION

This invention is in the field of fluorinated compounds useful as monomers in making fluoropolymers.

BACKGROUND OF THE INVENTION

There is an increasing demand for functionalized fluoromonomers and polymers to be applied in the areas of adhesion enhancement, cured coatings, interface compatibilizers for compounding/blending, and so on. Known cure site monomers such as $CF_2=CFOCF_2CF(CF_3)OCF_2CF_2-CN$ (U.S. Pat. 4,281,092) used in perfluoroelastomers require high temperature and the presence of catalysts to complete the curing. Hence, the direct utilization of such functional monomers in fluoroplastics is generally inconvenient to use and not practical.

Thus, there is an unfilled need for a convenient functional monomer for use in fluoropolymers.

SUMMARY OF THE INVENTION

This invention provides a compound having the formula $$CF_2=CF-R_f-(CH_2)_n-OP(O)_p-\Phi_2 \qquad (I)$$

wherein n is 1–3, p is 0 or 1, $R_f$ is perfluoroalkyl or perfluoroalkoxy having 1–20 carbon atoms, $\Phi$ is bromine, chlorine, or OM, and M is H, $NH_4$ or alkali metal.

Polymers comprising units derived from compound (I) are also provided. Preferred polymers contain units derived from at least one other fluoromonomer. The presence in such polymers of units derived from (I) can transform the normally chemically inert fluoropolymer into a reactive fluoropolymer to enhance its adhesion to other materials.

Aqueous dispersions, solutions in highly fluorinated solvents, and coatings of the phosphorus-containing fluoropolymers are further embodiments of the invention.

DETAILED DESCRIPTION

It has been discovered that compounds having the general formula $$CF_2=CF-R_f-(CH_2)_n-OP(O)_p-\Phi_2 \qquad (I)$$

wherein n is 1–3, p is 0 or 1, $R_f$ is linear or branched perfluoroalkyl or perfluoroalkoxy having 1–20 carbon atoms, $\Phi$ is bromine, chlorine or OM, and M is H, $NH_4$ or alkali metal, are useful as monomers in making fluoropolymers, and are particularly useful in minor amount to introduce highly reactive functional side groups into the fluoropolymer. Such fluoropolymers are useful materials in the areas of adhesion enhancement, coatings, thermosetting resins, grafting polymers, curable elastoplastics and elastomers, and the like.

In compound (I), preferably n=1. Preferred $R_f$ are perfluoroalkoxy having 2–20 carbon atoms, including $[O-CF_2CF(CF_3)]_k-O-CF_2CF_2$ wherein k=1–5, most preferably k=1, and $O-(CF_2)_m$ wherein m=2–20, most preferably m=2–4. When $R_f$ is $(CF_2)_j$, j=2–12. Preferably, j=2–8. When $\Phi$ is OM, a preferred M is H or $NH_4$.

The phosphorus-containing compound (I) of this invention exhibits a desirable combination of properties. The functional group $-OP(O)_p-\Phi_2$ has sufficient stability to survive polymerization processes, aqueous when $\Phi$ is OM, non-aqueous when $\Phi$ is chlorine or bromine. However, (I) is thermally active enough to provide rapid crosslinking at moderate temperatures, even without catalyst, making it useful, for example, as a crosslinking site in polymers. Additionally, the functionality of (I) can be used to provide fluoropolymers, which are normally non-adherent, with adhesive properties. In either case, the functional comonomer units in the copolymer may be changed from the original comonomer, but are nevertheless derived therefrom.

The unusual temperature response of (I) has several implications for utility, such as when used as a monomer incorporated into fluoropolymers. Because of its high thermal activity, (I) can be very useful in polymer resins that are fabricated without high temperature exposure before shaping, as in powder coating or in deposition from solution or aqueous dispersion, or in polymers that can be shaped by melt processing techniques at relatively low temperature and subsequently cured, such as for low-melting polymers or for elastomeric polymers.

Phosphorus-containing compounds (I) of this invention can be prepared in high yield by a process in which compounds having the general formula $$CF_2=CF-R_f-(CH_2)_n-OH \qquad (II)$$

are reacted with $P(O)_pCl_3$ or $P(O)_pBr_3$ wherein n, p and $R_f$ are as defined above, either neat or in aprotic solvent, to obtain the chloride or bromide, e.g., $$CF_2=CF-R_f-(CH_2)_n-OP(O)_p(Cl_2) \qquad (III)$$

followed by hydrolysis to obtain the acid $$CF_2=CF-R_f-(CH_2)_n-OP(O)_p-(OH)_2 \qquad (IV)$$

The acid can be further reacted with ammonium or alkali metal base to obtain the corresponding salt. Starting compounds (II) are known, and are disclosed, for example, in U.S. Pat. Nos. 4,564,717 and 5,059,720. Aprotic solvents that can be used include, for example, tetrahydrofuran and methylene chloride. Preferably, the reaction is carried out neat, i.e., without solvent. In carrying out the reaction of (II) with phosphoryl chloride to obtain (III), it is preferred for the phosphoryl chloride to be present in an amount in excess of the amount of (II) on a molar basis. Large excesses of phosphoryl chloride, e.g. 2× or 5×, can be used and are preferred, but are not necessary. The reaction can be carried out at atmospheric pressure under essentially anhydrous conditions. The reaction is faster at elevated temperature, and reaction temperature in the range 50°–150° C. is desirable, with temperature of 90°–130° C. preferred. The presence of a small amount of anhydrous metal salt in the reaction mass is beneficial, but is not required. The excess phosphoryl chloride can be recovered by distillation at atmospheric pressure, and the higher-boiling product (III) can then be recovered by distillation at reduced pressure.

Hydrolysis of the bromide or chloride product (III) to obtain the acid (IV) can be carried out simply by contacting (III) with water for a period of time sufficient to complete the hydrolysis. Agitation of the hydrolyzing mixture is desirable to promote good contact of (III) with the water. The hydrolysis reaction can conveniently be carried out at ambient temperature, or can be accelerated by moderate heating. After completion of hydrolysis, HCl resulting from hydrolysis along with any residual water can be removed under heat and vacuum.

Polymers of this invention comprise units derived from the phosphorus-containing monomer (I) of this invention. Preferred polymers of this invention contain units derived from at least one other fluorinated monomer, though such polymers can also contain units derived from fluorine-free monomers.

Fluorinated monomers that can be used include fluoroolefins having 2–10 carbon atoms, fluorinated dioxoles, and fluorinated vinyl ethers of the formula $CY_2=CYOR$ or $CY_2=CYOR'OR$ wherein Y is H or F, and —R, and —R'— are independently completely-fluorinated or partially-fluorinated alkyl and alkylene groups containing 1–8 carbon atoms. Preferred —R groups contain 1–4 carbon atoms and are preferably perfluorinated. Preferred —R'— groups contain 2–4 carbon atoms and are preferably perfluorinated.

Preferred fluoroolefins have 2–6 carbon atoms and include TFE, HFP, CTFE, vinyl fluoride, vinylidene fluoride, trifluoroethylene, hexafluoroisobutylene, and perfluorobutyl ethylene. Preferrec, cyclic fluorinated monomers include perfluoro-2,2-dimethyl-1,3-dioxole (PDD) and perfluoro-2-methylene-4-methyl-1,3-dioxolane (PMD). Preferred fluoropolymers include the group of tetrafluoroethylene (TFE) polymers. Preferred TFE polymers include perfluoropolymers, particularly copolymers of TFE and one or more of perfluoroolefins having 3–8 carbon atoms, especially hexafluoropropylene (HFP), and perfluoro(alkyl vinyl ethers) having alkyl groups containing 1–5 carbon atoms, especially 1–3 carbon atoms. Preferred fluoropolymers also include melt-fabricable copolymers of ethylene and TFE or chlorotrifluoroethylene, which copolymers can also contain up to 10 mol % of one or more additional monomers.

Copolymerizable fluorine-free monomers that can be used in conjunction with the phosphorus-containing monomers of this invention and at least one other fluorinated monomer include, for example, ethylene, propylene, n-butylene, isobutylene, vinyl acetate, and vinyl ethers such as methyl vinyl ether.

Such fluoropolymers can be glassy, plastic, or elastomeric. They can be amorphous or partially crystalline, melt-fabricable or non-melt-fabricable. Melt-fabricable fluoropolymer resins, usually having melt viscosity of up to about $1 \times 10^5$ Pa.s as customarily measured, are usually considered to be extrudable or injection-moldable. The fluoropolymers of this invention are normally solid at 15°–20° C. and can have any molecular weight (MW) suitable for the intended use. Generally, the weight average MW is at least 50,000 and can range up to much higher values, such as 1,000,000 and even higher.

For fluoropolymers of this invention comprising (I) and at least one other fluorinated monomer, units derived from compounds (I) are usually minor components of the polymers of this invention. Generally, the amount of (I) is in the range 0.02–10 mol % based on total monomer units in the polymer. Preferably, the amount of (I) is 0.02–5 mol %, most preferably 0.02–3 mol %.

The identity and proportion in the polymer of units derived from other monomers, fluorinated and fluorine-free, can have wide.ranges depending on the physical, chemical, or electrical properties sought. Thus, the polymers of this invention can be plastic or elastomeric, generally according to the identity and proportion of units derived from monomers making up the major part of the polymer composition, as known in the art.

Polymers of this invention can be prepared by any of the known processes for making fluoropolymers. Such processes can be conducted, for example, in an aqueous or non-aqueous medium, or in mixed media, i.e., hybrid processess, as well known in the art. As likewise well known in the art, dispersion or suspension processes can be employed, and processes can be conducted on a batch, semi-batch, or continuous basis.

The phosphorus-containing compounds (I) wherein $\Phi$ is OM (M=H, $NH_4$, or alkali metal) have surfactant properties. Consequently, when a polymer containing units derived from (I) is made by aqueous dispersion polymerization, the compound (I) can function as a monomeric surfactant, i.e. acting to stabilize the dispersion as well as incorporating into the polymer. Thus, the amount of other dispersing agent used in the polymerization can be reduced or eliminated, depending on how much phosphorus-containing monomer surfactant (I) is used. For this effect, M=H or $NH_4$ is preferred.

The halide embodiment of (I), i.e., $\Phi$=Br or Cl, can be used in non-aqueous polymerization to obtain polymers having pendant phosphorus halide groups. Alternatively, it is possible to use the halide monomer in aqueous polymerization and obtain polymer with side groups containing the acid, i.e., to hydrolyze, for example, $—OP(O)_pCl_2$ to $—OP(O)_p(OH)_2$ during the polymerization process.

The phosphorus-containing polymers of this invention can be used in dispersion form. When produced by dispersion polymerization, the aspolymerized (raw) dispersion may be used as discharged from the reactor if it has adequate stability and/or wetting characteristics for the intended purpose. Alternatively, the raw dispersion can be adjusted by addition of surfactants, or concentrated and stabilized by techniques well known in the art. Dispersion concentrations can vary over a broad range, such as from about 10 wt % solids as obtained from polymerization to about 70 wt % solids when concentrated, based on combined weight of polymer solids and aqueous medium. The phosphorus-containing polymer of the present invention as an aqueous dispersion is another embodiment of the invention.

Alternatively, traditional techniques known in the art (see U.S. Pat. No. 5,266,639, for example) can be used to recover the phosphorus-containing fluoropolymer of this invention from the aqueous polymerization medium. For example, such methods as coagulation by vigorous agitation, optionally with added electrolyte, or by freezing and thawing, followed by separation of the wet solids from the liquid and then by drying can be used.

As one skilled in the art will recognize, particles of the fluoropolymers of this invention can be used in many ways. Particles or particle aggregates, for example, can be sprinkled or dusted into place, can be applied to a surface from a dispersion or slurry, can be mixed with other powder or liquid as a binder or for other purposes, or can be distributed on a surface by one of several powder coating techniques such as electrostatic spraying or fluidized bed coating.

Phosphorus-containing fluoropolymers of this invention can be in solution in highly fluorinated solvents. Illustrative solvents are disclosed, for example, by Tuminello & Cavanaugh in U.S. Pat. No. 5,328,946 and by Morgan et al. in U.S. Pat. No. 5,397,829. Other solvents that can be used include fluorinated trialkyl amines such as perfluoro(dibutylmethyl)amine and perfluoro(triamyl)amine. Lower-melting polymers are more easily dissolved than higher-melting polymers, and amorphous polymers are even more easily dissolved. Solutions of the phosphorus-containing fluoropolymers of this invention in highly fluorinated solvents are another aspect of the invention. Perfluorinated compounds are preferred as solvents, but fluorinated compounds having up to about 12.5 atomic percent (at %) hydrogen and/or about 37.5 at % chlorine, based on total atoms bonded to carbon atoms, can be used. Generally, at least 50% of total atoms bonded to carbon atoms will be fluorine atoms. The concentration of polymer in the solutions of this invention can be at least 0.1 wt % and as much as 10 wt % and higher, 20 wt % and 30 wt %, depending on the solubility of the polymer in the solvent, based on combined weight of polymer and solvent. Since solution viscosity increases with polymer concentration, lower concentrations, such as 0.5–5 wt %, are preferred for many purposes.

Dispersions and solutions of the phosphorus-containing polymers of this invention can be used according to any of the techniques by which such systems are known to be used, including casting, dipping, painting and spraying, making it possible to achieve end results that could not be achieved with previously available perfluoropolymers or could be achieved only in less convenient ways. These results include any of the results for which polymer dispersions and solutions are used, such as coating, encapsulation, and impregnation. Normally, the dispersion or solution is deposited in place in the wet state, the deposit is dried, and the dried resin is fused or consolidated thermally.

The phosphorus-containing fluoropolymer dispersions and solutions of this invention can be used to make coatings on a broad range of substrate materials, including metals, semiconductors, glass, ceramics, refractory materials, dielectric materials, carbon or graphite, wood, and natural and synthetic polymers including plastics and elastomers. The substrates can be in a broad range of physical forms, including film or paper, foil, sheet, slab, coupon, wafer, wire, fiber, filament, cylinder, sphere, and other geometrical shapes, as well as in a virtually unlimited number of irregular shapes. These coatings can be useful for articles requiring anti-reflective, chemical resistant, release, lubricity, anti-staining, ice release, low dielectric constant, or reduced surface energy characteristics. Coatings can be applied by methods known in the art, including dipping, spraying, and painting. For plane substrates of suitable dimensions, spin coating can be employed. Porous substrates, including those made from fluoropolymer such as polytetrafluoroethylene, can also be coated or impregnated. These include, for example, screens, foams, microporous membranes, and woven and non-woven fabrics.

Coatings of the phosphorus-containing polymers of this invention can be a sole coating on a substrate, or a component of a multilayer coating. For example, a phosphorus-containing fluoropolymer coating of this invention can be used as a first or primer, intermediate, or final (top) coating in a multilayer fluoropolymer coating system. One or more layers of a multilayer system can contain fluoropolymer other than the polymer of this invention, and can be dispersion or powder coatings. The coatings of this invention include coatings resulting from several successive applications of dispersion or solution to increase coating thickness to desired levels.

Coatings of this invention can consist of the phosphorus-containing fluoropolymers of this invention alone, or of the phosphorus-containing polymers admixed with minor amounts of other materials either soluble in water or the solvent or dispersed in the coating dispersion or solution. A minor amount can be up to about 10 wt %, or up to 20 wt % or 25 wt %, based on the combined weight of phosphorus-containing fluoropolymer and additive.

Coatings of this invention can contain phosphorus-containing fluoropolymers of this invention admixed with other fluoropolymer that is free of units derived from compound (I). Other fluoropolymer can be non-functional, i.e., also free of other functional monomer. Such fluoropolymers can be as described above for fluoropolymers of the present invention but without the phosphorus-containing monomer. Preferred such fluoropolymers include the group of TFE polymers, including TFE homopolymers and the copolymers of TFE and one or more of perfluoroolefins having 3–8 carbon atoms, especially hexafluoropropylene (HFP), and perfluoro(alkyl vinyl ethers) having alkyl groups containing 1–5 carbon atoms, especially 1–3 carbon atoms. When other fluoropolymer is admixed with the phosphorus-containing fluoropolymer of the present invention, other fluoropolymer may be present in major amount, including amounts comparable to and even greatly exceeding the amount of the polymer of the invention. For example, other fluoropolymer can be present in amounts several times, e.g., 3, 6, 9 or 10 times or more, the amount of phosphorus-containing fluoropolymer. That is, for example, the amount of other fluoropolymer can be up to 20 parts by weight, preferably up to 15 parts, and most preferably up to 10 parts, for each weight part of phosphorus-containing fluoropolymer. Such large amounts of other fluoropolymer can serve to alter the properties of the coating, for example, to change the coefficient of friction or to modify the mechanical properties of the coating. When other fluoropolymer is present in such large amounts, the phosophorous-containing fluoropolymer serves as a binder. I.e., even in such small proportions, the phosphorus-containing fluoropolymer acts to adhere other fluoropolymer, including non-functional fluoropolymer, to dissimilar material. Other fluoropolymer present can be similar to the phosphorus-containing fluoropolymer, aside from the presence of units derived from compound (I), or can be quite different. Differences can, for example, lie in composition, i.e., in monomers present and/or their proportions, in molecular weight (or melt viscosity), in some combination of the foregoing, and the like. As an illustration, the phosphorus-containing fluoropolymer can be a melt-fabricable TFE copolymer while other fluoropolymer can be a melt-fabricable TFE copolymer containing the same non-functional comonomer in different amount and having different melt viscosity. As a further illustration, the phosphorus-containing fluoropolymer can be an amorphous copolymer while other fluoropolymer can be a non-melt-fabricable TFE homopolymer.

One skilled in the art will recognize that there are numerous ways of combining materials for preparation of coatings comprising phosphorus-containing fluoropolymer and other fluoropolymer, including powder blends, dispersion blends, suspensions of micropowders in dispersion or solution, and the like. In another embodiment, this invention provides a fluoropolymer blend composition, comprising fluoropolymer containing units derived from compound (I) and other fluoropolymer that is free of units derived from compound (I). Fluoropolymer powder used as a component of the blend composition of the invention usually has average particle size in the range 1–100 $\mu$m, more commonly in the range 5–50 $\mu$m.

Specific coated articles are within the scope of this invention.

Coated articles include cookers and frypans, oven liners, and the like.

Coated articles include valves, wire, metal foil, shoe molds, snow shovels and plows, ship bottoms, chutes, conveyors, dies, tools, industrial containers, molds, lined reactor vessels, automotive panels, heat exchangers, tubing, and the like.

Coated articles include c-rings, gaskets, seals, beading, windshield wipers, and automotive window and door seals, rubber rolls for photocopiers and laser printers including fuser and pressure rolls, rubber belts for photocopiers, and the like.

Coated articles include shower doors, oven and microwave glass, lenses, head lamps, mirrors, automobile windshields, cathode ray tubes such as used in television sets and computer monitors, laboratory glassware, and vials for pharmaceuticals.

Coated articles include flat panel displays such as liquid crystal displays and light emitting diodes, photoconductor rolls for photocopiers and laser printers, electronic devices wherein coatings are interlayer dielectrics, photomasks, and the like.

Coated articles include statuary, architectural panels and buildings, and the like.

EXAMPLES

Melting temperature ($T_m$) and glass transition temperature ($T_g$) were measured by differential scanning calorimetry (DSC), using a DuPont thermal analyzer. As is conventional, $T_m$ was taken as the peak of the melting endotherm for partially-crystalline polymers, while $T_g$ was taken as the point of Elope change in the DSC trace for non-crystalline polymers.

Polymer composition was measured by high temperature $^{19}F$ NMR spectroscopy using a GE NMR spectrometer. Temperature was such that the sample was in the melt state, that is, above $T_m$ for partially-crystalline samples and above $T_g$ for non-crystalline samples.

Monomer compositions were determined by proton and $^{19}F$ NMR, infrared spectroscopy (IR), and gas chromatography (GC).

Example 1

CF$_2$=CFO—CF$_2$CF(CF$_3$)O—CF$_2$CF$_2$—CH$_2$—OP(O)—Cl$_2$ and CF$_2$=CF—CF$_2$CF$_2$—CH$_2$CH$_2$—OP(O)—Cl$_2$ A pre-dried flask was charged with 9,9-dihydro-9-hydroxy-perfluoro(3,6-dioxa-5-methyl-1-nonene) (EVE-OH, U.S. Pat. No. 5,059,720) (257 g, 0.652 mol), phosphoryl chloride (500 g, 3.257 mol) and anhydrous calcium chloride (3.6 g, 0.0324 mol). This reaction mixture was heated at 110° C. for 6–8 hr or until the EVE-OH starting material was consumed. The excess phosphoryl chloride was recovered by distillation at normal pressure (bp 105°–108° C.). The residual liquid was then distilled under reduced pressure to give the 9-phosphonochloride-9,9-dihydro-perfluoro(3,6-dioxa-5-methyl-1-nonerie) (EVE-P-chloride, formula above) product as a clear, colorless liquid having a boiling point of 85°–90° C. at 5 mmHg (or 67°–72° C. at 2 mmHg). Yield: 200 g (60%).

When CF$_2$=CF—CF$_2$CF$_2$—CH$_2$CH$_2$—OH (Example 2, U.S. Pat. No. 4,564,717) is used in the above procedure instead of EVE—OH, CF$_2$=CF—CF$_2$CF$_2$—CH$_2$—CH$_2$—OP(O)—Cl$_2$ is obtained as the phosphorus-containing compound (I).

Example 2

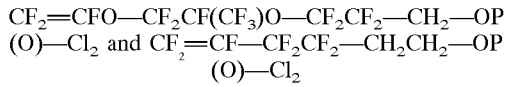

A round bottom flask was charged with 700 g (1.37 mol) of EVE-P-chloride (Example 1) and water (49.4 g, 2.75 mol) was slowly added. After all the water was added, the reaction mixture was stirred vigorously at ambient temperature overnight. Then, product was placed under high vacuum at 60° C. to remove any residual water and gave 9-phosphono-9,9-dihydro-perfluoro(3,6-dioxa-5-methyl-1-nonene) (EVE-P, formula above) product as a clear, viscous liquid (640 g, 98,6% yield).

When CF$_2$=CF—CF$_2$CF$_2$—CH$_2$CH$_2$—OP(O)—Cl$_2$ is used in the above procedure instead of EVE-P-chloride, the phosphono compound CF$_2$=CF—CF$_2$CF$_2$—CH$_2$CH$_2$—OP(O)—(OH)$_2$ is obtained as the phosphorus-containing compound (I).

Example 3

Copolymerization of EVE-P with TFE

A 400 mL stainless steal shaker table was charged with de-ionized water (280 mL), ammonium perfluorononanoate surfactant (C-9, 2.0 g), disodium phosphate (2.0 g), EVE-P (4.0 g, Example 2), and ammonium persulfate (APS, 0.6 g). The tube was sealed, cool-evacuated, then TFE (45 g, 0.45 mol) was transferred into the tube. The tube was sealed and heated at 70° C. for 4 hrs. After cooling, the resulting polymer latex was coagulated with dilute nitric acid. The polymer formed was collected by filtration, then washed thoroughly with warm water. After drying in a vacuum oven (150 mmHg) at 100° C. overnight, a white polymer powder (44.0 g) was obtained. This polymer was exhibited a $T_m$ at 344.6° C. (1st heat curve) and a $T_m$ at 329.2° C. (2nd heat curve) as measured by DSC. The molar composition of this polymer was determined to be TFE/EVE-P=99.1/0.9 by $^{19}F$ NMR spectroscopy at polymer melt state.

Example 4

Copolymerization of EVE-P with TFE

The procedure of Example 3 was essentially repeated, except that the amount of C-9 was 1.5 g and the amount of EVE-P was 8.0 g. After drying, 42.0 g of a white polymer powder were obtained. This polymer exhibited a $T_m$ at 343.2° C. (1st heat) and a $T_m$ at 331.8° C. (2nd heat) as measured by DSC. The composition of this polymer was determined to be TFE/EVE-P=98.0/2.0 (molar) by $^{19}F$ NMR spectroscopy at polymer melt state.

Example 5

Copolymerization of EVE-P with TFE and PPVE

The procedure of Example 4 was essentially repeated, except that 5.0 g of PPVE were added to the charge to the shaker tube. The amount of dried white polymer powder weighed 47.5 g. This polymer exhibited a broad melting endotherm with $T_m$ at 311.0° C. (2nd heat) and with low heat of fusion as measured by DSC. The molar composition of this polymer was determined to be TFE/PPVE/EVE-P=93.64/2.94/3.42 by $^{19}F$ NMR spectroscopy at polymer melt state (350° C.).

Example 6

TFE/PEVE copolymer with EVE-P in shell

In a horizontal 1-gal (3.8-L) autoclave equipped with a paddle agitator, 2100 mL of demineralized water were deaerated by evacuation and purging with nitrogen. While under vacuum, 25 g of a 20 wt % solution of ammonium perfluorooctanoate (C-8), 17 mL of perfluoro(ethyl vinyl ether) (PEVE) and 1 g of ethane were added. The temperature was increased to 80° C. and the pressure was increased to 300 psig (2.17 MPa) by addition of TFE. An initial initiator charge of 60 mL of a 2 g/L aqueous solution of APS was added. At kickoff, as determined by a 5 psi (0.03 MPa) pressure drop, a feed of a mixture of TFE and PEVE in the ratio TFE:PEVE=97.1:2.9 by weight was begun to maintain pressure at 300 psig. Also, an addition of 0.5 mL/min of the same initiator solution was begun. When 600 g of TFE/PEVE mixture had been added after kickoff, 10 mL of EVE-P in 300 mL of demineralized water were added. After 650 g of TFE/PEVE mixture had been added after kickoff, all feeds were stopped and the pressure was allowed to drop to 150 psig (1.1 MPa). The reactor was vented and cooled, and the product dispersion was collected. Solids content of the dispersion was 22.2 wt %. An aliquot of the dispersion was placed in a freezer and allowed to freeze solid overnight. Upon thawing, the resulting suspension was filtered through Whatman 541 paper on a Bucherer funnel and washed three times with demineralized water. The solids were then dried overnight at 100° C. Melting point was 313° C. as determined by DSC. The product copolymer resin contained 1.97 wt % of PEVE and 0.23 wt % of EVE-P, as determined by Fourier transform infrared (FTIR) spectroscopy which had been calibrated by $^{19}$F NMR. The melt flow rate, as measured at 372° C. with a 1060 g weight, was 12 g/10 min.

A portion of the powder solids was suspended in isopropanol to form a thin slurry (5 g in 15 mL alcohol). The slurry was coated onto an aluminum sheet using a #24 wire-wound rod (R. D. Specialties, Inc.) and the alcohol allowed to air dry. Average coating density was determined to be about 2.2 mg/cm$^2$. Pellets of a TFE/PPVE copolymer resin that has been chemically modified to enhance purity and improve thermal stability (Teflon® PFA fluoropolymer resin grade 440 HP, DuPont) were placed on the coating in a 0.010-inch (0.25-mm) thick and 6-inch (15.2-cm) square chase having a 4-inch (10.2-cm) square opening and another aluminum sheet was placed on top of the construction. The sandwich was compression molded at 350° C. in an 8-min cycle (3 min at platten contact, 2 min to increase ram force to 5000 lb {2273 kg}, and 3 min at 5000 lb), removed from the press quenched in ice water. The aluminum sheet on the 440 HP side of the construction easily peeled from the resin surface.

The powder treated side remained adhered to the aluminum. A 1-inch (2.54-cm) wide strip of this adhered side was cut and subjected to peel testing in an Instron tensile tester. Average peel strength was 1.5 lb/inch (270 g/cm), showing the enhanced adhesion of the polymer of this invention.

Example 7 and Control A

TFE/PMVE/PEVE/EVE-P Copolymer

The autoclave used in Example 6 was charged with 2200 mL of demineralized water and deaerated by evacuation and purging with nitrogen as before. With no pressure in the reactor 5 g of C-9 and 15 mL of EVE-P were added. The temperature was increased to 90° C., and the pressure was increased to 400 psig (2.86 MPa) by addition of a mixture of 27.2 wt % TFE, 51 wt % perfluoro(methyl vinyl ether) (PMVE), and 21.8 wt % PEVE. An initial charge of 30 mL of a 6.0 g/L solution of APS in water was added. At kickoff, as determined by a 10 psi (0.07 MPa) pressure drop, the same initiator solution was fed at the rate of 3.25 mL/min and a monomer mixture having the composition TFE/PMVE/PEVE=62/23/15 by weight was fed to maintain pressure at 400 psig. After about 600 g of monomer had been added after kickoff, all feeds were stopped. When the pressure dropped to 250 psig (1.83 MPa), the reactor was vented and the product dispersion was collected. Solids content of the dispersion was 24.3 wt %. The polymer was isolated by vigorously mixing the dispersion with approximately 40 mL of 70% nitric acid solution, and filtering with a plain weave filter cloth. The wet resin was rinsed with demineralized water three times with vigorous agitation, and dried at 80° C. under vacuum. The product resin contained 54.0 wt % of TFE, 30.4 wt % of PMVE, and 15.6 wt % of PEVE and EVE-P combined, as determined by $^{19}$F NMR. The amount of EVE-P in the copolymer was less than 1 wt %. No crystalline melting point was detected by DSC. The weight average molecular weight as measured by SEC viscometry was 205,000.

The same procedure was essentially followed to make a TFE/PMVE/PEVE copolymer (Control A), except that EVE-P was omitted, the APS initiator solution concentration was 1.5 g/L, and the initiator solution pumping rate after kickoff was 2 mL/min. Solids content of the raw dispersion was 22.3 wt %. The composition of the product resin was TFE/PMVE/PEVE=56.3/29.9/13.8 by weight as determined by $^{19}$F NMR. No crystalline melting point was detected by DSC. The weight average molecular weight as measured by SEC viscometry was 279,000.

Example 8

Adhesion to Rubber

A 5 wt % solution, based on combined weight of polymer and solvent, of the TFE/PMVE/PEVE/EVE-P copolymer of Example 7 in Fluorinert® FC-40 (3M), predominanly perfluoro(dibutylmethyl)amine, was prepared. Strips (2 cm×8 cm) of compounded and cured silicone rubber (Mid-Atlantic Rubber Co, Raleigh, N.C.) were dipcoated in this solution and dried at 100° C. for 30 min, leaving a glossy coating on the rubber substrate approximately 4–5 µm thick. The surface energy of the sample was analyzed by measuring the contact angle of hexadecane on the surface using the sessile drop method. The advancing angle was 64° indicating a fluoropolymer surface. The sample was then subjected to a pull using Scotch® brand B98 adhesive tape according to the procedure of ASTM D-3359, except that the coating was not cross-hatched and boiling water was not used. The coating was unaffected by the tape pull. Repeated rubbing with the tip of a cotton swab failed to remove the coating, indicating that the coating was very durable. When the procedure was repeated with the TFE/PMVE/PEVE copolymer of Control A, most of the coating was removed by a tape pull or by rubbing with a cotton swab.

The above procedure was repeated using strips of compounded and cured nitrile rubber, ethylene/propylene/diene rubber (Nordel® hydrocarbon rubber grade 1320, DuPont Dow Elastomers), and fluoroelastomer (Viton® A, DuPont Dow Elastomers) as the substrate for the TFE/PMVE/PEVE/EVE-P copolymer coating. All coatings on these rubber substrates were durable, as indicated by tape and cotton swab testing as above.

A silicone rubber strip was also coated with TFE/PMVE/PEVE/EVE-P copolymer resin using the aqueous dispersion as collected from the reactor. Similar results were obtained, indicating the utility of aqueous dispersion of this invention for application of a coating on a substrate.

A 9.5×4×0.25 inch (24.1×10.2×0.6 cm) piece of red silicone rubber was cleaned with 2-propanol and coated with a 5% solution of TFE/PMVE/PEVE/EVE-P copolymer in FC-40 using a doctor blade. The coating was air dried. A second piece of silicone rubber was similarly cleaned and air dried. The dynamic coefficient of friction (COF) of these two samples were measured according to ASTM D-1894 using a 257 g sled. The COF of the coated sample was 1.09, while the COF of the uncoated sample was 3.21.

Example 9

Adhesion to Copper

A 2 wt % solution, based on combined weight of polymer and solvent, of the TFE/PMVE/PEVE/EVE-P copolymer of Example 7 in FC-40 was prepared. Squares (3 cm×3 cm) of copper foil (Alfa, 0.254 mm thick, 99.9% metals basis) were cut and cleaned with dichloromethane. These squares were then spin-coated (500 rpm) with the solution and dried at 100° C. for 30 min, leaving a dull red/orange finish and a coating having thickness of approximately 1.0–1.4 µm on the copper substrate. The advancing angle for hexadecane in the sessile drop method was 62°. The sample was then subjected to tape pull as in Example 8, except that the coating was X-cut rather than cross hatched. As prepared, the coating was unaffected by the tape pull. After placing the sample in boiling water for 15 min and allowing it to cool, the tape test was repeated and the coating was again unaffected. When the procedure was repeated with the TFE/PMVE/PEVE copolymer of Control A, the coating was unaffected by the tape pull prior to exposure to boiling water. After immersing the sample in boiling water, the coating was removed from approximately 25% of the surface by the tape pull.

Example 10

Adhesion to Stainless Steel

A 3-cm square stainless steel coupon was dipcoated with the 5 wt % TFE/PMVE/PEVE/EVE-P copolymer solution described in Example 8, and the coating was dried at 100° C. for 30 min. Coating thickness was approximately 0.8 µthick. After cooling, the coated coupon was subjected to the same contact angle and tape tests outlined in Example 9. The advancing contact angle was measured to be 70°. The coating was unaffected by the tape pull, both as prepared and after immersion in boiling water. When the procedure was repeated with a 5 wt % solution of the TFE/PMVE/PEVE copolymer of Control A, the coating was removed from the entire surface by the tape pull, without exposure to boiling water.

Example 11

Adhesion to Nickel

A 3-cm square coupon of nickel metal (Alfa, 0.787 mm thick, 99.5% metals basis) was spin-coated essentially as described in Example 9, resulting in a TFE/PMVE/PEVE/EVE-P copolymer coating approximately 1.5 µthick on the nickel substrate. After cooling, the coating was subjected to the same contact angle and tape tests outlined in Example 9. The advancing contact angle was measured to be 71°. The coating was unaffected by the tape pull, both as prepared and after immersion in boiling water. When the procedure was repeated with the TFE/PMVE/PEVE copolymer of Control A, the coating was removed from the entire surface by the tape pull, without exposure to boiling water.

Example 12

COF of Coating Containing Other Fluoropolyner

Four 9.5×4×0.25 inch pieces of red silicone rubber were coated using a doctor blade with 3% or 5% solutions of TFE/PMVE/PEVE/EVE-P copolymer (P-polymer) in FC-40 containing polytetrafluoroethylene (PTFE) powder (Zonyl® fluoroadditive grade MP 1400, DuPont) in amounts given in Table 1. The coatings were air dried, and COF was measured as described in Example 8. Table 1 shows that coatings of TFE/PMVE/PEVE/EVE-P containing other fluoropolymer (PTFE) in increasing amounts have reduced COF.

TABLE 1

Compositions and Results for Example 12

| P-polymer:PTFE (wt) | COF |
|---|---|
| 10:2 | 0.921 |
| 10:3 | 0.536 |
| 10:4 | 0.438 |
| no coating | 2.23 |

Example 13

Adhesion of Dispersion Blend to Silicone Rubber

Two aqueous dispersions A and B, formulated as shown in Table 2 by blending P-polymer dispersion (21 wt % solids) prepared generally as in Example 7 and a TFE/HFP copolymer (FEP) dispersion formulation (46 wt % FEP, Teflon® FEP Industrial Coating grade 856–200, DuPont), were sprayed on 3×0.75×0.125 inch (7.6×1.9×0.3 cm) cleaned silicone rubber strips and cured at 280° C. for 10 min. The sprayed (wet) thickness was approximately 0.5 mil (0.013 mm). After cooling, the coating had a smooth appearance and had good surface lubricity, and the coating could not be removed by a tape pull or by rubbing hard with a finger. As a comparison, a third dispersion was similarly formulated but without the addition of TFE/PMVE/PEVE/EVE-P copolymer dispersion. This formulation was sprayed on silicone strips and heated in a similar manner. The resulting coating showed good durability, but poor adhesion to the silicone substrate as the coating could be removed by a finger rub. This demonstrates that the phosphorus-containing fluoropolymer of the present invention effectively adheres other fluoropolymer (non-functional) to silicone rubber when other fluoropolymer is present in major amount.

TABLE 2

Dispersion Blend Formulations

| | Formulation (wt %) | |
|---|---|---|
| Component | A | B |
| FEP | 22.99 | 27.06 |
| P-polymer | 10.50 | 8.65 |
| Liquid | 66.51 | 64.29 |

Example 14

Adhesion of Dispersion/Powder Blend to Silicone Rubber

Two aqueous dispersions C and D containing FEP dispersion particles, TFE/PMVE/PEVE/EVE-P copolymer (P-polymer) dispersion particles, and FEP powder in the approximate ratios of 2:1:2 and 1:2:1 by weight, respectively, were formulated as shown in Table 3 by blending the P-polymer dispersion and FEP dispersion used in Example 13 and an FEP powder obtained by grinding a commercial powder (Teflon® FEP fluoropolymer resin grade TE-9050, DuPont) to an average particle size of approximately 15 pm. The formulations were sprayed onto cleaned pressure rolls (22 cm long and 2 cm in diameter) having silicone rubber surfaces. The coated rolls were cured at 280° C. for 20 min and cooled. The resulting coatings had a slight orange peel appearance and good lubricity. The coating had good adhesion and was very durable, and could not be removed by repeated rubbing with a finger or cotton swab or by a tape pull.

TABLE 3

Dispersion/Powder Blend Formulations

| | Formulation (wt %) | |
|---|---|---|
| Component | C | D |
| FEP (disp.) | 18.40 | 8.16 |
| P-polymer | 8.82 | 15.61 |
| FEP powder | 18.00 | 7.96 |
| Liquid | 54.78 | 68.27 |

Example 15

Adhesion of Multi-coat System on Silicone Copier Roll

A silicone pressure roll as described in Example 14 was sprayed with a thin coating of an aqueous dispersion of TFE/PMVE/PEVE/EVE-P copolymer (21% solids) prepared generally as in Example 7. The sprayed thickness (wet) was approximately 0.3 mil (0.0076 mm). The coating was dried at 150° C. for 5 min and then at 20° C. for 10 min. The roll was topcoated using an aqueous co-dispersion of PTFE and TFE/PPVE copolymer (20 wt % fluoropolymer solids), and cured using infra red radiation with a maximum surface temperature of 750° F. (399° C.). After cooling, the coated roll had a smooth appearance and good lubricity. The coating had good adhesion and was very durable, and could not be removed by repeated rubbing with a finger or a metal key. This example demonstrates that aqueous dispersions of the phosphorus-containing fluoropolymer of the invention can be used as primers for fluoropolymers.

Example 16

Adhesion of Blend Composition to Silicone Copier Roll

Two formulations, E and F, consisting of FEP powder dispersed into a solution of TFE/PMVE/PEVE/EVE-P copolymer (P-polymer) in Fluorinert® FC-75 (3M) were made according to the Table 4. The P-polymer was made generally as in Example 7, while the FEP powder was the same as used in Example 14. The powder was mixed well into the solutions and the mixture was brush-coated onto cleaned silicone pressure rolls as described in Example 14. The coated rolls were cured at 300° C. for 30 min and cooled. The resulting coatings had a slight orange peel appearance, good lubricity and good durability. Attempts to remove the coating using ten repeated tape pulls were unsuccessful. These results illustrate that blend compositions containing large amounts of other fluoropolymer relative to the amount of phosphorus-containing fluoropolymer can be used in coatings.

TABLE 4

Solution/Powder Blend Formulations

| | Formulation (wt %) | |
|---|---|---|
| Component | E | F |
| P-polymer | 1.98 | 1.69 |
| FEP powder | 0.99 | 15.25 |
| FC-75 | 97.03 | 83.05 |

Example 17

Adhesion of Multi-coat System to Silicone Copier Roll

A silicone rubber pressure roll as described in Example 14 was brushed coated with a 2% solution of TFE/PMVE/PEVE/EVE-P copolymer (prepared generally as in Example 7) in FC-75 and air dried. A topcoat of FEP powder (DuPont grade 532-8000) was sprayed onto the coated roll, and the resulting roll was cured at 300° C. for 30 min. After cooling, the coated roll had a smooth appearance and good lubricity. Attempts to remove the coating using ten repeated tape pulls were unsuccessful. The coating had good durability and was difficult to scratch using a pair of metal tweezers. Damage to the silicone rubber was observed when tweezers were used in an attempt to remove the coating, illustrating the high degree of adhesion achieved with the phosphorus-containing fluoropolymer of this invention.

Example 18

TFE/HFP/VF Copolymer with EVE-P in Shell

A clean 2-gal (7.4-L) horizontal autoclave equipped with an agitator was charged with 4300 mL of demineralized water and 50 g of a 20 wt % solution of C-8, and deaerated by evacuation and purging with nitrogen as before. Then, the autoclave was alternately pressured (10–20 psig, 0.17–0.24 Mpa) with TFE and evacuated three times. After the temperature was increased to 90° C. and with the agitator turning at 80 rpm, the pressure was increased to 450 psig (3.21 MPa) by addition of a mixture of TFE, HFP, and vinyl fluoride (VF) having the composition TFE/HFP/VF=50/44/6 by weight (453 g). Then, a 2.0 g/L solution of APS in water was added at the rate of 25 mL/min for 5 min and thereafter at the rate of 1 mL/min for the duration of the run. After kickoff, as determined by a 10 psi (0.07 MPa) pressure drop, a monomer mixture having the composition TFE/HFP/VF= 65/10/25 by weight was fed to maintain pressure at 450±5 psig. After 800 g of the monomer mixture had been added after kickoff, a solution of 15 mL of EVE-P in 50 mL of $C_5H_2F_{10}$ was added at the rate of 10 mL/min for 5 min (50 mL total). After 1000 g of monomers had been added over 99 min after the start of APS addition, all feeds were stopped, the reactor was vented, and 5690 g of milky white product dispersion were collected. Solids content of the dispersion was 17.1 wt %. The polymer was isolated by freezing and thawing, and filtering with a plain weave filter cloth. The wet resin was rinsed with demineralized water three times with vigorous agitation, and dried at 80° C. under vacuum.

The product resin contained 64.9 wt % of TFE, 11.7 wt % of HFP, and 23.4 wt % of VF as determined by $^{19}F$ NMR, while the presence of EVE-P was indicated by laser ablation induction-coupled mass spectrometry. The copolymer had a crystalline melting point of 169° C. with heat of fusion of 11.4 J/g.

Example 19

Amorphous TFE/HFP/VF/EVE-P Copolymer

The procedure of Example 18 was essentially followed, except that the EVE-P solution was precharged following the TFE pressure/evacuation procedure, the precharged monomer mixture was TFE/HFP/VF=9/88/3 by weight (924 g), and the makeup monomer mixture was TFE/HFP/VF=30/46/24 by weight. The time to add 1000 g of monomers after the start of APS addition was 174 min. The resultant dispersion (5775 g) was clear with a light blue tint and contained 19.2 wt % solids. The composition of the copolymer was TFE/HFP/VF=29.0/48.8/22.2 by weight as determined by $^{19}$F NMR while the presence of EVE-P was indicated by laser ablation induction-coupled mass spectrometer. The resin was amorphous, as indicated by a glass transition temperature of 5° C. –11° C. and the absence of a crystalline melting point by DSC analysis.

Example 20

TFE/HFP/CTFE/EVE-P Copolymer

The procedure of Example 19 was essentially followed, except that the aqueous charge was 4400 mL, the amount of EVE-P was 45 g, the EVE-P was introduced into the aqueous charge by dissolving the EVE-P in 45 g of $C_5H_2F_{10}$ and adding the resultant solution to 2000 mL of the aqueous charge at 55° C. and then flashing off the $C_5H_2F_{10}$, 18 g of Zonyl® TBS fluorosurfactant (DuPont) were used instead of C-8, CTFE was used instead of VF, the precharged monomer mixture was TFE/HFP/CTFE=16/58/25 by weight, the makeup monomer mixture was TFE/HFP/CTFE=66/21/13 by weight, the APS solution concentration was 20.0 g/L, the APS solution feed rates were 20 mL/min for 3 min and thereafter 0.5 mL/min for the duration of the run. The time to add 742 g of monomers after the start of APS addition was 164 min, at which point feed was stopped. The composition of the copolymer was TFE/HFP/CTFE/EVE-P=65.8/8.8/25.0/0.4 by weight as determined by $^{19}$F NMR.

What is claimed is:

1. A coated article comprising a substrate coated with a coating, wherein said coating comprises a fluoropolymer comprising units derived from the compound having the formula

wherein n is 1–3, p is 0 or 1, $R_f$ is perfluoroalkyl or perfluoroalkoxy having 1–20 carbon atoms, Φ is bromine, chlorine, or OM, and M is H, $NH_4$ or alkali metal.

2. The coated article of claim 1, wherein said substrate is metal.

3. The coated article of claim 1, wherein said substrate is polymer.

4. The coated article of claim 3, wherein said polymer is elastomer.

5. The coated article of claim 1, wherein said coating contains other fluoropolymer that is free of units derived from the compound of claim 1.

6. The coated article of claim 1, wherein the amount of said other fluoropolymer is up to 20 parts by weight for each weight part of said fluoropolymer comprising units derived from the compound of claim 1.

7. The coated article of claim 1, wherein said substrate is a copier roll having a silicone rubber surface.

* * * * *